United States Patent
O'Donovan

(10) Patent No.: US 10,485,956 B2
(45) Date of Patent: Nov. 26, 2019

(54) GUIDE EXTENSION CATHETER WITH GROOVED PUSH MEMBER SEGMENT

(71) Applicant: Medtronic Vascular, Inc., Santa Rosa, CA (US)

(72) Inventor: Conor O'Donovan, Galway (IE)

(73) Assignee: Medtronic Vascular, Inc., Santa Rosa, CA (US)

(*) Notice: Subject to any disclaimer, the term of this patent is extended or adjusted under 35 U.S.C. 154(b) by 21 days.

(21) Appl. No.: 15/615,668

(22) Filed: Jun. 6, 2017

(65) Prior Publication Data

US 2017/0354800 A1    Dec. 14, 2017

Related U.S. Application Data

(60) Provisional application No. 62/347,115, filed on Jun. 8, 2016.

(51) Int. Cl.
  *A61M 25/06* (2006.01)
  *A61M 25/00* (2006.01)
  *A61M 25/01* (2006.01)

(52) U.S. Cl.
  CPC .... *A61M 25/0662* (2013.01); *A61M 25/0043* (2013.01); *A61M 25/0102* (2013.01); *A61M 2025/0681* (2013.01)

(58) Field of Classification Search
  CPC .......... A61M 25/0662; A61M 25/0043; A61M 25/0102; A61M 25/01; A61M 25/09; A61M 2025/0681; A61M 25/0905
  See application file for complete search history.

(56) References Cited

U.S. PATENT DOCUMENTS

| | | | |
|---|---|---|---|
| 2012/0150271 A1* | 6/2012 | Fischell | A61M 25/09 623/1.11 |
| 2013/0197483 A1* | 8/2013 | Anderson | A61M 25/0105 604/528 |
| 2014/0276618 A1* | 9/2014 | Di Caprio | A61M 25/0068 604/510 |
| 2015/0151090 A1 | 6/2015 | Sutton et al. | |

FOREIGN PATENT DOCUMENTS

| EP | 1639951 A1 | 3/2006 |
|---|---|---|
| WO | 96/01604 A1 | 1/1996 |

OTHER PUBLICATIONS

PCT/US2017/036233, The International Search Report and the Written Opinion of the International Searching Authority, dated Sep. 7, 2017, 14pgs.

* cited by examiner

*Primary Examiner* — Kami A Bosworth
*Assistant Examiner* — Alexandra Lalonde
(74) *Attorney, Agent, or Firm* — Shumaker & Sieffert, P.A.

(57) ABSTRACT

A guide extension catheter includes a push member and a distal shaft. The push member includes a segment having a first surface and a second surface opposite the first surface. The segment includes a groove in the first surface. The second surface is substantially flat. The distal shaft is coupled to the push member and includes a passageway. The segment of the push member including the groove is adjacent to the distal shaft.

16 Claims, 9 Drawing Sheets

GUIDE EXTENSION CATHETER WITH GROOVED PUSH MEMBER SEGMENT

CROSS REFERENCE TO RELATED APPLICATIONS

This application claims the benefit under 35 U.S.C. § 119(e) of the filing date of U.S. Provisional Application No. 62/347,115 filed Jun. 8, 2016, the contents of which are incorporated by reference herein in their entirety.

FIELD OF THE INVENTION

The invention relates to a guide extension catheter for use with a guide catheter and an interventional coronary device. More specifically, the present invention relates to a guide extension catheter having a groove in a push member, wherein the groove guides an interventional coronary device into a distal shaft of the guide extension catheter.

BACKGROUND OF THE INVENTION

Arteries of the heart, and more specifically coronary arteries, may sometimes be occluded or narrowed by atherosclerotic plaques or other lesions. These afflictions are generally referred to as coronary heart disease or a stenosis, and result in inadequate blood flow to distal arteries and tissue. Heart bypass surgery may be a viable surgical procedure for certain patients suffering from coronary heart disease. However, traditional open surgery may inflict significant patient trauma and discomfort and require extensive recuperation times. Further, life threatening complications may occur due to the invasive nature of the surgery and the necessity for stoppage of the heart during such a surgery.

To address these concerns, efforts have been made to perform interventional cardiology procedures using minimally invasive techniques. In an example, percutaneous transcatheter (or transluminal) delivery and implantation of interventional coronary devices are employed to overcome the problems presented by traditional open surgery. In such a procedure, a guide catheter is first inserted through an incision into a femoral (transfemoral), or radial (transradial) artery of a patient. For example, the Seldinger technique may be utilized in either method for percutaneously introducing the guide catheter. In such methods, the guide catheter is advanced through the aorta and inserted into the opening of an ostium of a coronary artery. A guidewire, or other interventional coronary devices, such as a catheter mounted stent and/or balloon catheter, may be introduced through the guide catheter and maneuvered/advanced through the vasculature and the stenosis of the diseased coronary artery. However, when attempting to pass through a difficult stenosis, or when conducting a radial intervention using a small diameter guide catheter, the guide catheter may not have adequate back support, and continued application of force to advance the interventional coronary device though the stenosis may cause the distal end of the guide catheter to dislodge from the opening of the ostium of the coronary artery, resulting in potential damage to the surrounding tissue.

In order to prevent the guide catheter from dislodging, interventional cardiologists sometimes would deep seat the guide catheter into the coronary artery. The term "deep seat" or "deep seating" means that the guide catheter would be pushed farther downstream into the coronary artery. However, deep seating the guide catheter risks the guide catheter damaging the coronary artery wall (dissection or rupture), occluding the coronary artery, and interfering with blood flow to the coronary artery.

One attempt to provide additional support to a guide catheter that has gained acceptance is the use of a guide extension catheter. The guide extension catheter is deployed within a lumen of the guide catheter and extends distally from the distal end of the guide catheter into the coronary artery. Their smaller size, as compared to the guide catheter, allows the guide extension catheter to be seated more deeply in the coronary artery with less potential damage. The guide extension catheter provides additional support to the guide catheter to aid in delivery of interventional coronary devices. In cases with a difficult stenosis or radial interventions, the use of the guide extension catheter reduces the risk of dislodging the guide catheter from the opening of the ostium of the coronary artery during treatment. However, their smaller size may pose difficulty in receiving an interventional coronary device within the passageway of the distal shaft of the guide extension catheter. As an example, an interventional coronary device such as a catheter with a stent mounted on an outer surface of a balloon may catch, snag, or otherwise become snared on the entry port of the distal shaft of the guide extension catheter.

Accordingly, there exists a need for an improved guide extension catheter that provides easier entry into the passageway of the distal shaft and reduces catching, snagging or snaring of interventional coronary devices advancing into the passageway.

BRIEF SUMMARY OF THE INVENTION

Embodiments hereof relate to a guide extension catheter including a push member and a distal shaft. The push member includes a segment having a first surface and a second surface opposite the first surface. The segment includes a groove in the first surface. The second surface of the segment is substantially flat. The distal shaft is coupled to the push member and includes a passageway. The segment of the push member including the groove adjacent the distal shaft.

Embodiments hereof further relate to a coronary treatment system including a guide extension catheter, a guide catheter, and an interventional coronary device. The guide extension catheter includes a push member and a distal shaft. The push member includes a segment having a first surface and a second surface opposite the first surface. The segment includes a groove in the first surface. The second surface of the segment opposite the groove is substantially flat. The distal shaft is coupled to the push member and includes a passageway configured to receive the interventional coronary device. The groove of the push member is configured to guide the interventional device into the passageway of the distal shaft. The guide catheter includes a lumen configured to receive the guide extension catheter and the interventional coronary device therethrough.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" and "distally" refer to positions distant from or in a direction away from the clinician. "Proximal" and "proximally" refer to positions near or in a direction toward the clinician.

The following detailed description is merely exemplary in nature and is not intended to limit the invention or the application and uses of the invention. Although the description of embodiments hereof are in the context of treatment of blood vessels such as the coronary arteries, the invention may also be used in any other body passageways where it is deemed useful. Furthermore, there is no intention to be bound by any expressed or implied theory presented in the preceding technical field, background, brief summary or the following detailed description.

Figure 1:
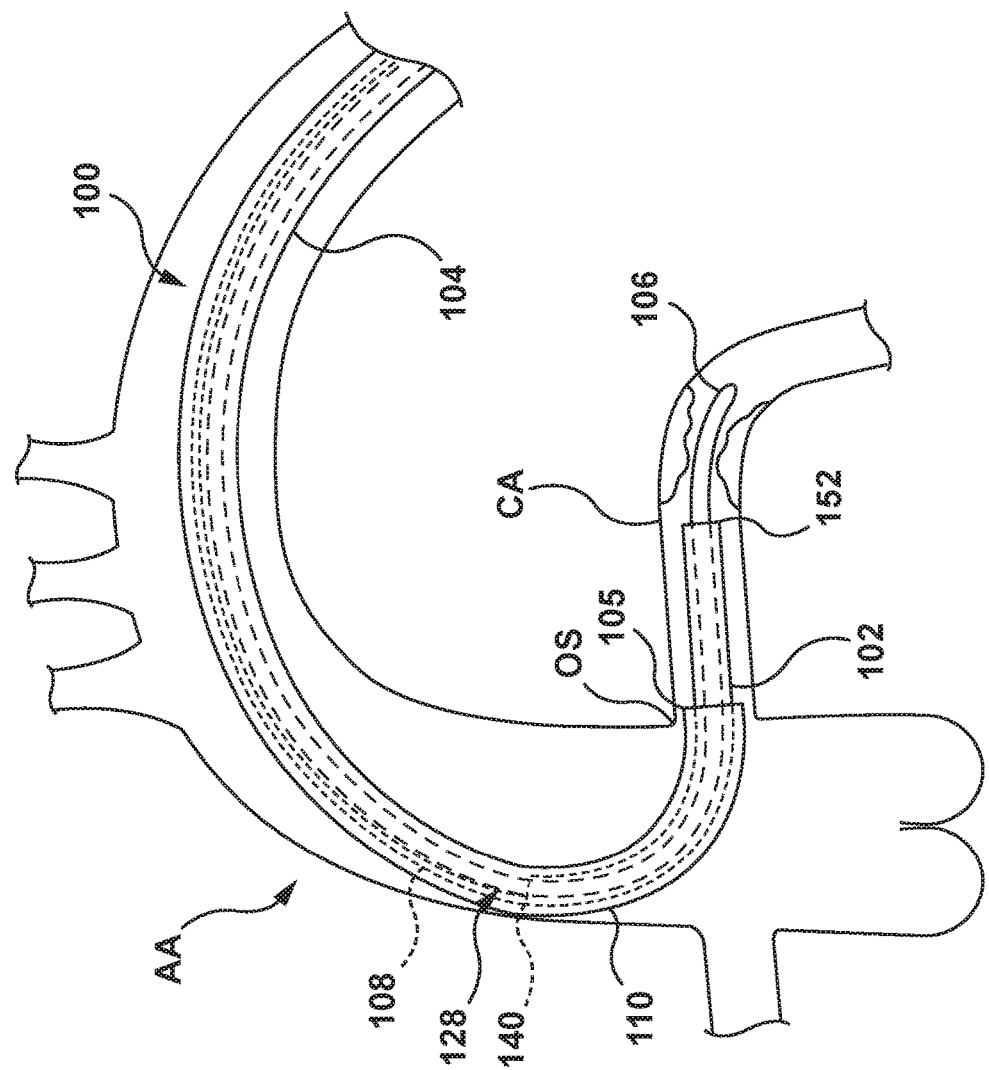
FIG. 1 depicts a sectional cut-away of an aorta and a coronary artery with a coronary treatment system disposed therein.

FIG. 1 illustrates a coronary treatment system 100 including a guide extension catheter 102, a guide catheter 104, and an interventional coronary device 106. The guide catheter 104 and the guide extension catheter 102 are configured to deliver the interventional coronary device 106 to a desired treatment location. In the embodiment shown in FIG. 1, the desired treatment location is in a coronary artery CA that is accessed through the aorta AA.

The guide catheter 104 may be utilized to access the aorta AA as shown in FIG. 1. Generally, the guide catheter 104 includes a lumen sized to receive an auxiliary device or devices (e.g. the guide extension catheter 102 and/or the interventional coronary device 106). The guide catheter 104 is configured to deliver the auxiliary device(s) such as the guide extension catheter 102 and the interventional coronary device 106 to a desired treatment location.

The interventional coronary device 106 may be any device suitable for treating an abnormal condition of a coronary artery, such as, but not limited to a stenosis. Non-limiting examples of interventional coronary device 106 include guidewires, balloon catheters, stent catheters, and FFR catheters.

Figure 2:
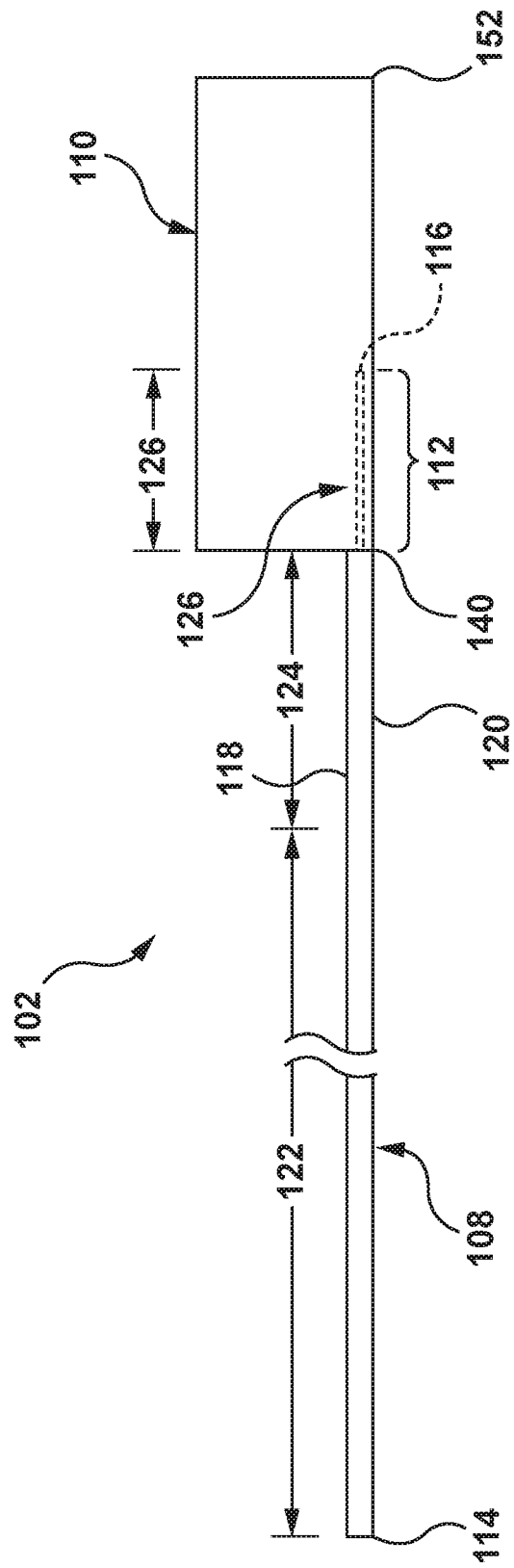
FIG. 2 depicts a side view of a guide extension catheter in accordance with an embodiment hereof.

FIGS. 2-8 illustrate the guide extension catheter 102 in accordance with an embodiment hereof. Referring to FIG. 2, the guide extension catheter 102 includes a push member 108 coupled to a distal shaft 110. The push member 108 is coupled to the distal shaft 110 at a transition joint 112. In an embodiment, the guide extension catheter 102 may be approximately 150 cm in length, with the distal shaft 110 of the guide extension catheter 102 being between 20 cm and 40 cm in length. However, this is not meant to limit the design and the guide extension catheter 102 and/or the distal shaft 110 thereof may be longer or shorter.

The push member 108, also referred to as a proximal shaft or pushwire, includes a proximal end 114 and a distal end 116. The push member 108 is configured to transfer motion applied at the proximal end 114 to the distal end 116. Further, the push member 108 is configured to transfer motion applied to the proximal end 114 to the coupled distal shaft 110 coupled to the push member 108. Stated more plainly, the push member 108 is configured such that movement of the push member 108 also moves the distal shaft 110.

In an embodiment, the push member 108 includes a proximal segment 122, an intermediate segment 124, and a distal segment 126. The proximal segment 122 extends distally from the proximal end 114 of the push member 108, the distal segment 126 extends proximally from the distal end 116 of the push member 108, and the intermediate segment 124 is disposed between the proximal segment 122 and the distal segment 126. The push member 108 may be formed of materials such as, but not limited to stainless steel, nickel-titanium alloys (e.g. NITINOL), high performance alloys that are cobalt, chromium, molybdenum and/or nickel based (e.g. MP35N, L605, ELGILOY), or other materials suitable for the purposes described herein.

Figure 3:
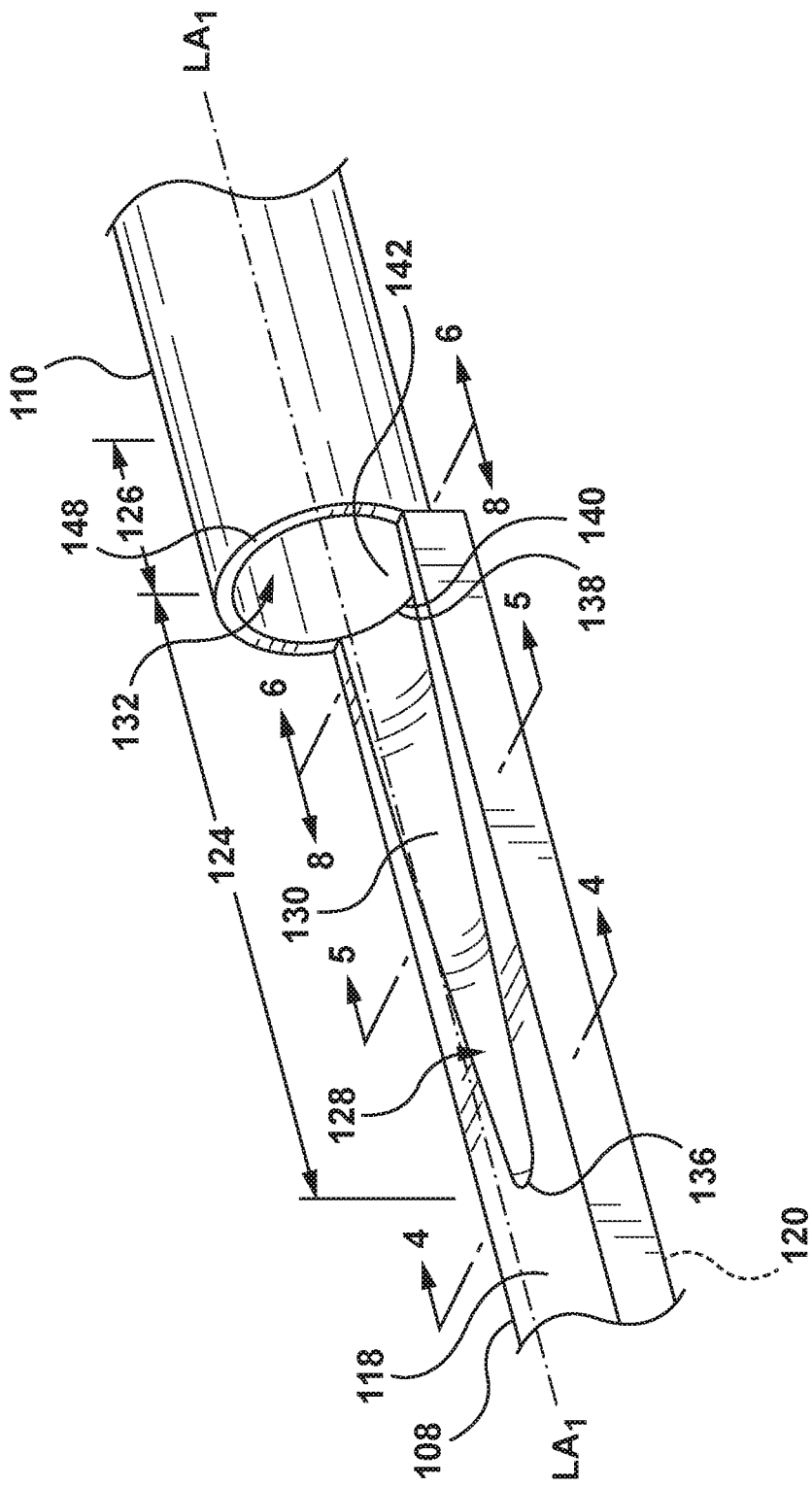
FIG. 3 depicts a perspective view of a portion of the guide extension catheter of FIG. 2.
Figure 3A:
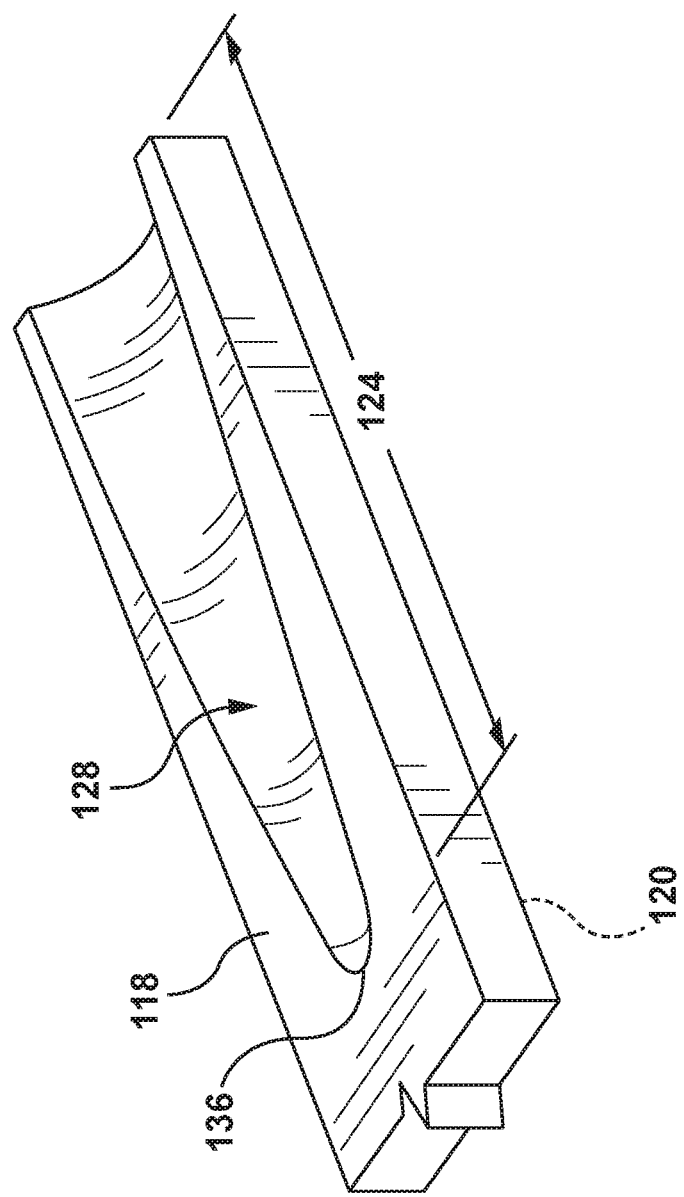
FIG. 3A depicts a perspective view of a portion of an intermediate segment of a push member of the guide extension catheter of FIG. 2.

As shown in FIGS. 3 and 3A, the intermediate segment 124 of the push member 108 is generally rectangular in cross-section, and includes a first surface 118 and a second surface 120 opposite the first surface 118. The first surface 118 and the second surface 120 are both substantially flat. The term "flat" as used herein means that the surfaces are horizontal or not curved such that if a flat surface were placed on a table, the flat surface and the table surface would be parallel. The term "substantially" or "generally" as used herein, particularly with respect to the term "flat", means within normal manufacturing tolerances. The proximal segment 122 may be generally rectangular in cross section, similar to the intermediate segment 124, but need not be. The proximal segment 122 may be other shapes in cross-section, such as generally circular, oval, oblong, or other shapes suitable for the purposes described herein.

Figure 6:
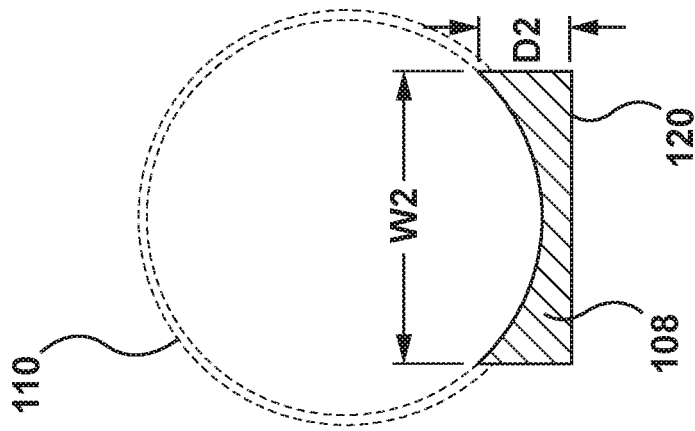
FIG. 6 depicts a cross-sectional view of the push member taken at line 6-6 of FIG. 2.
Figure 5:
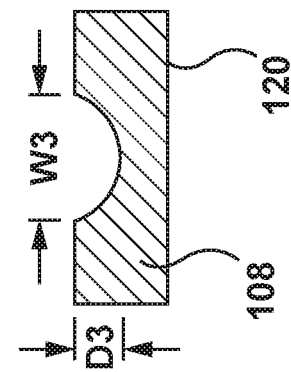
FIG. 5 depicts a cross-sectional view of the push member taken at line 5-5 of FIG. 2.
Figure 4:
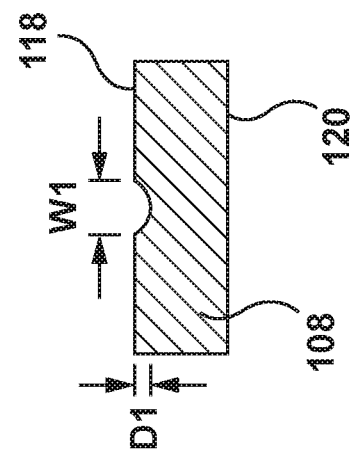
FIG. 4 depicts a cross-sectional view of the push member of the guide extension catheter taken at line 4-4 of FIG. 2.

As shown in FIGS. 3-6, the intermediate segment 124 of the push member 108 includes a groove 128 formed in the first surface 118. The groove 128 faces an extended central longitudinal axis LA1 of the distal shaft 110. The groove 128 is configured to guide the interventional coronary device 106 into a passageway 132 of the distal shaft 110. The groove 128 includes a proximal end 136 and extends distally to a distal end 138. The groove 128 is tapered from the distal end 138 to the proximal end 136. "Tapered" as used herein, means that the groove 128 becomes progressively smaller from the distal end 138 to the proximal end 136. In other words, the groove 128 becomes progressively larger from the proximal end 136 to the distal end 188. In the embodiment of FIGS. 3-6, the groove 128 has a first depth D1 and a first width W1 at the proximal end 136, as shown in FIG. 4, and a second depth D2 and a second width W2 at the distal end 138, as shown in FIG. 6. The first depth D1 is less than the second depth D2, and the first width W1 is less than the second width W2. Thus, as shown in FIGS. 4-6, which are cross-sectional illustrations of the intermediate segment 124 of the push member 108, the groove 128 begins at the proximal end 136 with the first width W1 and the first depth D1, and the groove 128 widens and deepens distally along the length of the groove 128. Thus, FIG. 5 shows an intermediate point between the proximal end 136 and the distal end 138 where the groove 128 has a third width W3 and a third depth D3, which are larger than the first width W1 and the first depth D2, respectively, but smaller than the second width W2 and the second depth D2, respectively. In an embodiment, the groove 128 widens and deepens linearly as the groove 128 extends distally. However, this is not meant be limiting, and the groove 128 may have other profiles, including non-linear profiles. In an embodiment, the first depth D1 of the groove 128 may be between 0.001 inch and 0.005 inch inclusive and the second depth D2 may be between 0.005 inch and 0.02 inch inclusive. By "inclusive" it is meant that the values at each end of the range are included in the range. In an embodiment, the first width W1 of the groove 128 may be between 0.001 inch and 0.005 inch inclusive and the second width W2 may be between 0.005 inch and 0.03 inch inclusive.

The groove 128 may be formed in the first surface 118 of the intermediate segment 124 of the push member 108 by methods such as, but not limited to a skiving/swaging process, laser removal process, other mechanical removal processes, or other processes suitable for the purposes described herein.

Figure 7:
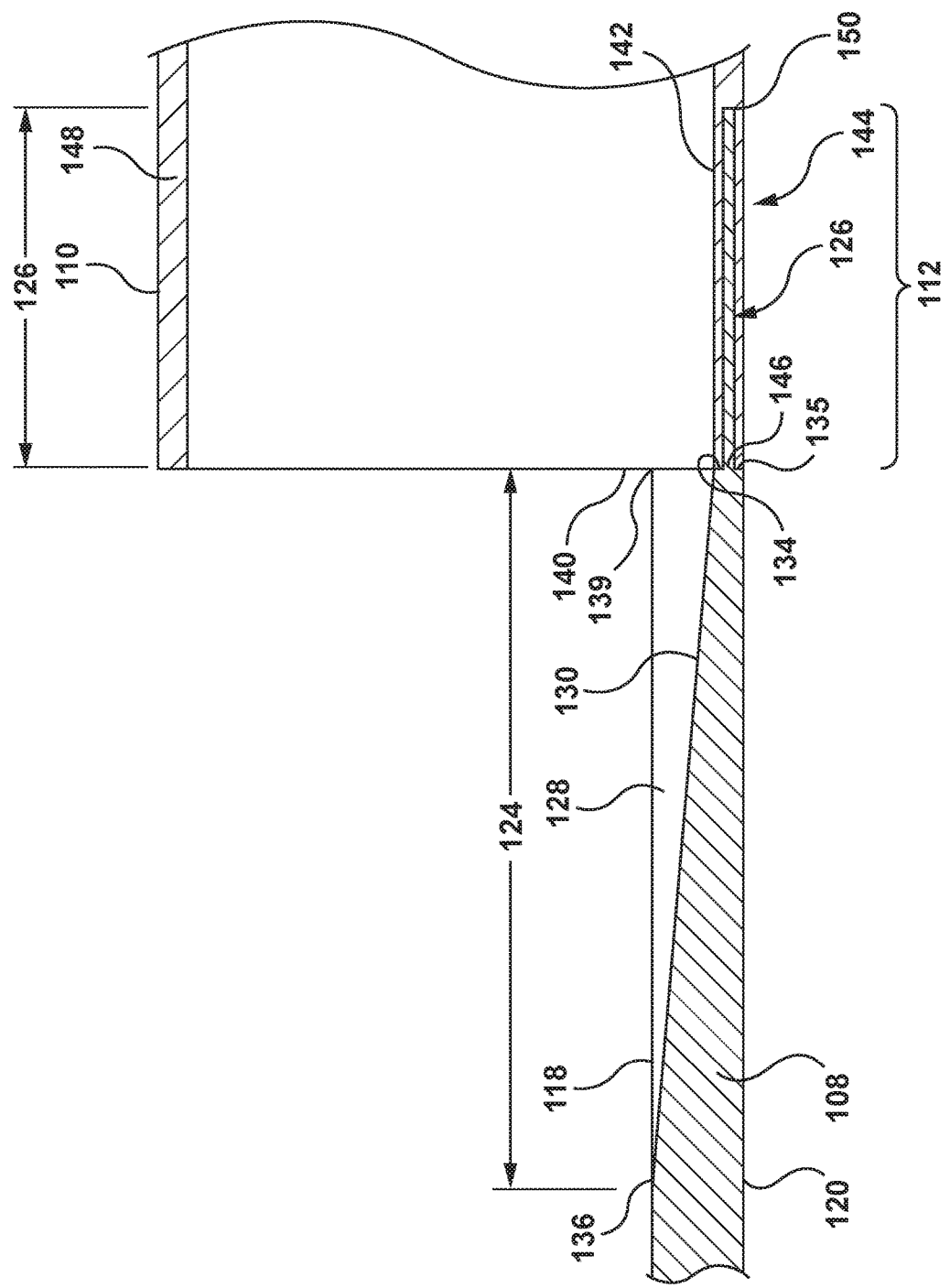
FIG. 7 depicts a longitudinal cross-sectional view of a distal portion of the guide extension catheter of FIG. 3 taken along a center-line of a groove in the push member.
Figure 7A:
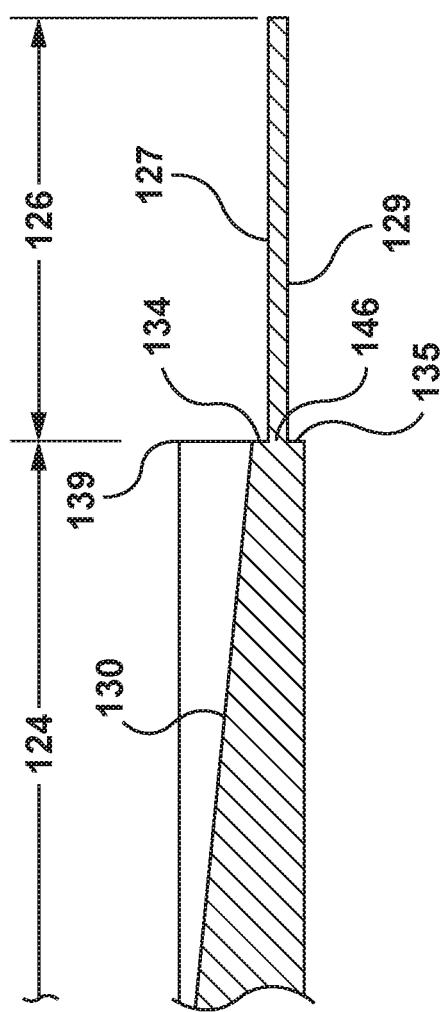
FIG. 7A depicts a longitudinal cross-sectional view of the intermediate and distal segments of the push member taken along a center-line of the groove in the push member.
Figure 8:
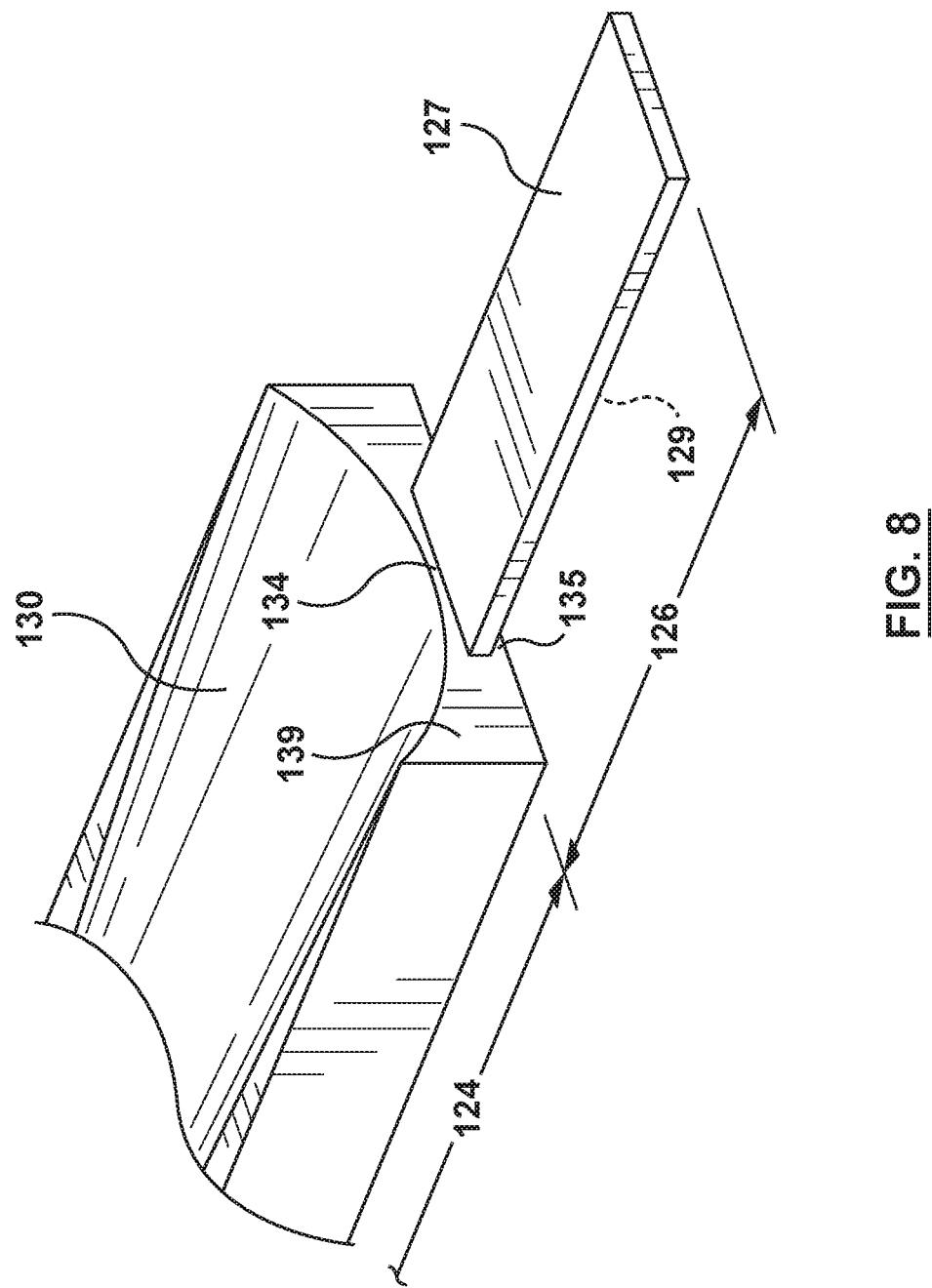
FIG. 8 depicts a perspective view of the push member of FIG. 2 taken from a distal end of the push member.

As shown in FIGS. 3 and 7, a surface 130 of the groove 128 at the distal end 138 of the groove 128 is aligned with an inner surface 142 of an adjacent portion of the distal shaft 110. An embodiment for enabling this alignment is shown in FIGS. 7, 7A, and 8. In particular, the distal segment 126 of the push member 108 extends distally from a distal end 139 of the intermediate segment 124. The distal segment 126 includes a proximal end 146 abutting the distal end 139 of the intermediate segment 124, and a distal end 150. In the embodiment shown in FIGS. 7, 7A, and 8, the distal segment 126 extends distally from the distal end 139 of the intermediate segment 124 such that a shoulder 134 is formed between the surface 130 of the groove 128 and an upper surface 127 of the distal segment 126. Stated another way, the shoulder 134 is formed where the distal end 139 of the intermediate segment 124 meets the proximal end 146 of the distal segment 126. In the embodiment of FIGS. 7, 7A, and 8, a shoulder 135 is also formed between the second surface 120 of the intermediate segment 124 and a lower surface 129 of the distal segment 126. The distal segment 126 of the push member 108 may be formed by a separate piece attached to the intermediate segment 124, or by methods such as, but not limited to, a laser removal process, machining, or other processes suitable for the purposes described herein. While the distal segment 126 is shown in FIG. 8 with a rectangular cross-section with a smaller width than the intermediate segment 124, this is not meant to limit the design and other cross-sectional shapes and widths of the distal segment 126 may be utilized. For example, and not by way of limitation, distal segment 126 may be curved to match the curvature of the distal shaft 110.

Although the proximal segment 122, the intermediate segment 124, and the distal segment 126 of the push member 108 have been described as a single component, this is not meant to be limiting. The proximal segment 122, the intermediate segment 124, and/or the distal segment 126 may be formed as separate components and coupled together to form the push member 108.

In an embodiment, the distal shaft 110 includes a proximal end 140 and a distal end 152. The distal shaft 110 is generally tubular and includes a wall 148 and the passageway 132, as shown in FIGS. 2, 3, 7, and 9. The passageway 132 is sized to receive the interventional coronary device 106. The distal shaft 110 may be formed of various materials, non-limiting examples of which include polymers and braided polymers.

In the embodiment of FIGS. 2-8, a transition joint 112 between the push member 108 and the distal shaft 110 includes the distal segment 126 of the push member 108 and a proximal portion 144 of the distal shaft 110. The transition joint 112 may be formed by overlapping the distal segment 126 of the push member 108 and the proximal portion 144 of the distal shaft 110, with the distal segment 126 disposed between layers of the distal shaft 110. The transition joint 112 is thus configured to couple the push member 108 to the distal shaft 110 and to transfer motion of the push member 108 to the distal shaft 110. In other embodiments, the distal segment 126 of the push member 108 may be attached to the distal shaft 110 such that the upper surface 127 of the distal segment 126 is attached to an outer surface of the wall 148 of the distal shaft 110, or such that the lower surface 129 of the distal segment 126 is attached to an inner surface of the wall 148. The distal segment 126 may be attached to the wall 148 via a mechanical bonding (e.g. adhesives, welding, thermal bonding, clips, etc.) or other bonds suitable for the purposes described herein.

Figure 9:
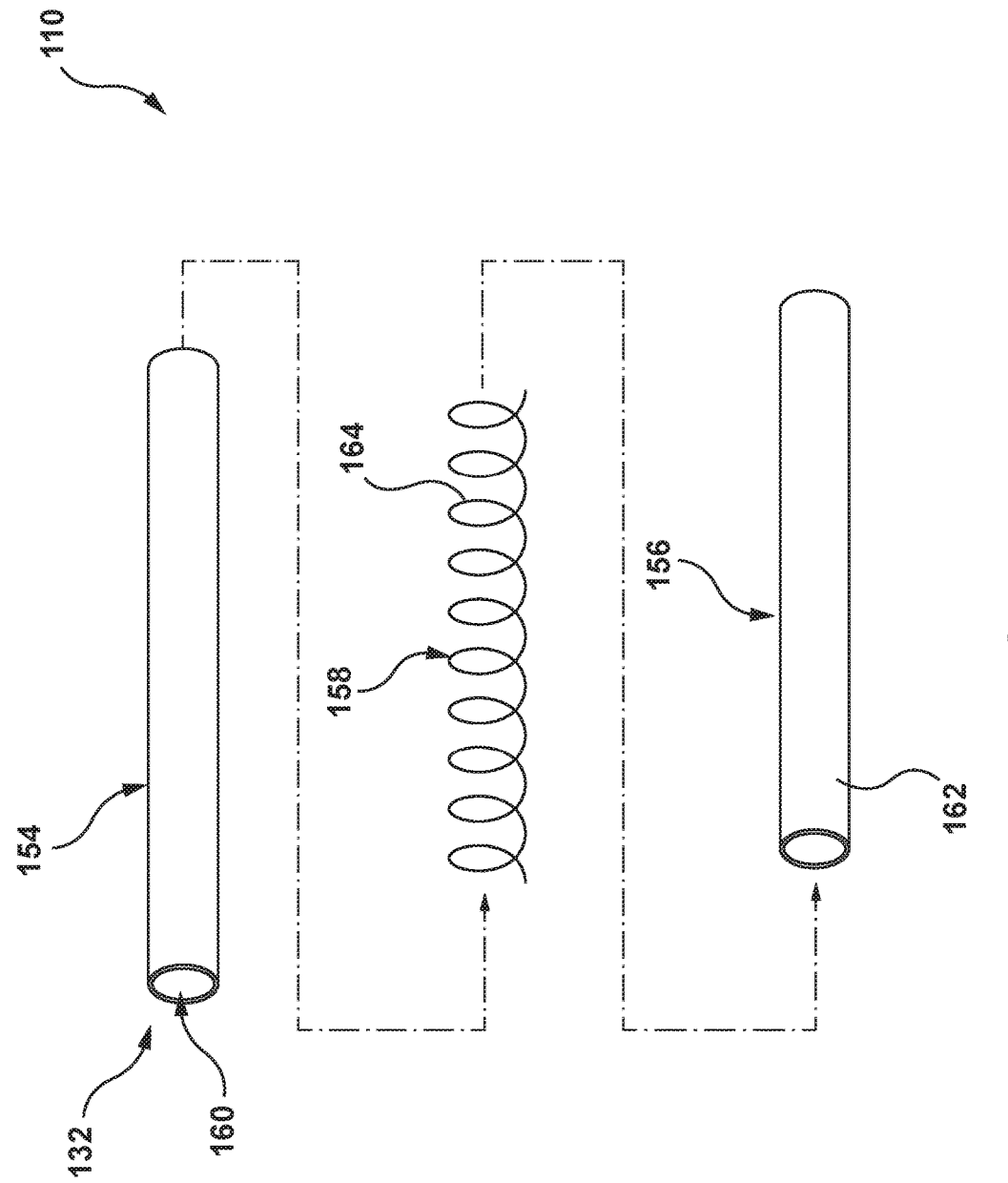
FIG. 9 depicts an exploded perspective view of an exemplary distal shaft of the guide extension catheter of FIG. 2.

FIG. 9 illustrates an example of the distal shaft 110, wherein the distal shaft 110 includes an inner liner 154, an outer jacket 156 and a support structure 158. The inner liner 154 is of a generally tubular shape and forms an inner surface 160 of the distal shaft 110. The inner liner 154 is configured to provide the distal shaft 110 with a low friction inner surface such that the interventional coronary device 106 may be advanced/retracted easily through the passageway 132 of the distal shaft 110. The inner liner 154 may be formed from materials such as, but not limited to polytetrafluoroethylene (PTFE), perfluoroalkoxy alkanes (PFAs), high-density polyethylene (HDPA), or other materials suitable for the purposes described herein. The outer jacket 156 is of a generally tubular shape and forms an outer surface 162 of the distal shaft 110. The outer jacket 156 is configured to provide flexibility to the distal shaft 110. The outer jacket 156 may be formed from materials such as, but not limited to, thermoplastic elastomers, such as but not limited to polyether block amides (e.g. PEBAX®, VESTAMID®), nylon, or other materials suitable for the purposes described herein. The support structure 158 is a generally tubular helically wound wire member 164 (also known as a filament). The support structure 158 is embedded between the inner liner 154 and the outer jacket 156. The support structure 158 is configured to provide strength and rigidity to the distal shaft 110. The support structure 158 may be bonded between the inner liner 154 and the outer jacket 156 by methods such as, but not limited to heat, fusion, adhesives, or other suitable methods. The support structure 158 may be formed from materials such as, but not limited to, stainless steel, nickel-titanium alloys (e.g. NITINOL), or other materials suitable for the purposes described herein.

Referring back to FIG. 1, a method for delivery the coronary interventional device to a desired treatment location may be described. The guide catheter 104 is advanced into the aorta AA and a distal end of the guide catheter 104 is disposed within an opening of an ostium OS of the coronary artery CA.

The guide extension catheter 102 is advanced through the guide catheter 104 until the distal end 152 of the distal shaft 110 is disposed distal of the distal end 105 of the guide catheter 104, and within the coronary artery CA proximal of the desired treatment location.

The interventional coronary device 106 is advanced through the guide catheter 104 adjacent or alongside the push member 108 of the guide extension catheter 102, as shown in FIG. 1. As the interventional coronary device 106 is advanced distally, a distal portion of the interventional coronary device 106 rides in the groove 128 (not visible in FIG. 1, but shown in FIG. 3) of the push member 108 of the guide extension catheter 102. The groove 128 guides the interventional coronary device 106 into the proximal end 140 of the distal shaft 110. More specifically, and as best shown in FIG. 7, an outer surface of the interventional coronary device 106 (visible in FIG. 1) may ride along the surface 130 of the groove 128. The outer surface 106 of the interventional coronary device 106 may be shaped similar to the groove 128 such that the interventional coronary device 106 is guided along the groove.

While various embodiments have been described above, it should be understood that they have been presented only as illustrations and examples of the present invention, and not by way of limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A guide extension catheter comprising:
   a push member including a proximal segment, an intermediate segment, and a distal segment, the intermediate segment having a first surface and a second surface opposite the first surface, wherein the intermediate segment includes a groove in the first surface, and wherein the second surface is substantially flat;
   a distal shaft coupled to the push member and including a passageway, wherein the intermediate segment of the push member including the groove is disposed adjacent the distal shaft; and
   a shoulder disposed between a distal end of the intermediate segment and a proximal end of the distal segment such that the shoulder is disposed between the first surface of the intermediate segment and an upper surface of the distal segment, and wherein the distal end of the intermediate segment defines a thickness greater than a wall thickness of the distal shaft.

2. The guide extension catheter of claim 1, wherein the groove in the first surface includes a proximal end having a first depth and a distal end having a second depth, wherein the first depth is less than the second depth.

3. The guide extension catheter of claim 2, wherein the proximal end of the groove has a first width and the distal end of the groove has a second width, wherein the first width is less than the second width.

4. The guide extension catheter of claim 3, wherein the first depth of the groove is between 0.001 inch and 0.005 inch inclusive and the second depth is between 0.005 inch and 0.02 inch inclusive.

5. The guide extension catheter of claim 3, wherein the first width is between 0.001 inch and 0.005 inch inclusive and the second width is between 0.005 inch and 0.03 inch inclusive.

6. The guide extension catheter of claim 1, wherein the groove in the first surface includes a proximal end having a first width and a distal end having a second width, wherein the first width is less than the second width.

7. The guide extension catheter of claim 6, wherein the first width is in the range of 0.001 inch and 0.005 inch inclusive and the second width is in the range of 0.005 inch and 0.03 inch inclusive.

8. The guide catheter of claim 1, wherein a distal end of the groove of the push member is aligned with an adjacent portion of an inner surface of the distal shaft.

9. The guide extension catheter of claim 1, wherein the distal segment overlaps with a proximal portion of the distal shaft to form a transition joint.

10. A coronary treatment system comprising:
    an interventional coronary device;
    a guide extension catheter including:
      a push member including a proximal segment, an intermediate segment, and a distal segment, the intermediate segment having a first surface and a second surface opposite the first surface, wherein the intermediate segment includes a groove in the first surface, and wherein the second surface is substantially flat;
      a distal shaft coupled to the push member and including a passageway, wherein the distal shaft is configured to receive the interventional coronary device; and
      a shoulder disposed between a distal end of the intermediate segment and a proximal end of the distal segment such that the shoulder is disposed between the first surface of the intermediate segment and an upper surface of the distal segment, and wherein the distal end of the intermediate segment defines a thickness greater than a wall thickness of the distal shaft; and
    a guide catheter including a lumen configured to receive the guide extension catheter and the interventional coronary device therethrough,
    wherein the groove of the push member is configured to guide the interventional device into the passageway of the distal shaft.

11. The coronary treatment system of claim 10, wherein the groove includes a proximal end having a first depth and a distal end having a second depth, wherein the first depth is less than the second depth.

12. The coronary treatment system of claim 11, wherein the proximal end of the groove has a first width and the distal end of the groove has a second width, wherein the first width is less than the second width.

13. The coronary treatment system of claim 12, wherein the first depth of the groove is in the range of 0.001 inch and 0.005 inch and the second depth is in the range of 0.005 inch and 0.02 inch.

14. The coronary treatment system of claim 12, wherein the first width is in the range of 0.001 inch and 0.005 inch and the second width is in the range of 0.005 inch and 0.03 inch.

15. The coronary treatment system of claim 10, wherein a distal end of the groove of the push member is aligned with an adjacent portion of an inner surface of the distal shaft.

16. The coronary treatment system of claim 10, wherein the distal segment overlaps with a proximal portion of the distal shaft to form a transition joint.

* * * * *